(12) United States Patent
Venturelli et al.

(10) Patent No.: US 8,778,010 B2
(45) Date of Patent: Jul. 15, 2014

(54) ENDOLUMINAL PROSTHESIS

(75) Inventors: Andrea Venturelli, Concesio (IT); Silvio Schaffner, Berlingen (CH)

(73) Assignee: Medtronic, Inc., Minneapolis, MN (US)

( * ) Notice: Subject to any disclaimer, the term of this patent is extended or adjusted under 35 U.S.C. 154(b) by 992 days.

(21) Appl. No.: 12/159,649

(22) PCT Filed: Feb. 17, 2006

(86) PCT No.: PCT/IT2006/000086
§ 371 (c)(1),
(2), (4) Date: Oct. 22, 2008

(87) PCT Pub. No.: WO2007/094020
PCT Pub. Date: Aug. 23, 2007

(65) Prior Publication Data
US 2009/0069882 A1    Mar. 12, 2009

(51) Int. Cl.
*A61F 2/06* (2013.01)

(52) U.S. Cl.
USPC ........................................................ 623/1.15

(58) Field of Classification Search
USPC .................... 623/1.15, 1.16, 1.34, 1.17, 23.7
See application file for complete search history.

(56) References Cited

U.S. PATENT DOCUMENTS

| | | | |
|---|---|---|---|
| 4,665,771 A | 5/1987 | Mitchell | |
| 4,665,905 A | 5/1987 | Brown | |
| 4,925,445 A | 5/1990 | Sakamoto et al. | |
| 6,416,539 B1 * | 7/2002 | Hassdenteufel | 623/1.15 |
| 2003/0045925 A1 | 3/2003 | Jayaraman | |
| 2003/0083736 A1 * | 5/2003 | Brown et al. | 623/1.16 |
| 2004/0243216 A1 * | 12/2004 | Gregorich | 623/1.15 |
| 2006/0025847 A1 * | 2/2006 | Parker | 623/1.15 |

FOREIGN PATENT DOCUMENTS

| | | |
|---|---|---|
| EP | 0888757 | 1/1999 |
| EP | 0928606 | 7/1999 |
| WO | 00/28922 | 5/2000 |
| WO | 2005/104991 | 11/2005 |

\* cited by examiner

*Primary Examiner* — Tuan V Nguyen
*Assistant Examiner* — Tin Nguyen (57) ABSTRACT

An endoluminal prosthesis comprises a tubular body which can be expanded about a longitudinal axis. A plurality of serpentines extend in a substantially circumferential direction. Each comprises arm portions and bend portions which join two subsequent arms. The bends facing an adjacent serpentine are circumferentially offset relative to the respective opposite bends of the contiguous serpentine, both when the prosthesis is collapsed and when the prosthesis is expanded. A first portion comprises at least two adjacent serpentines interconnected by at least one bridge, and at least two bends situated at the shortest longitudinal distance between the two serpentines is not connected by a bridge. A second portion comprises at least two adjacent serpentines interconnected by a number of bridges equal to the number of pairs of bends of the two serpentines, at the shortest longitudinal distance between the two serpentines.

21 Claims, 8 Drawing Sheets

ENDOLUMINAL PROSTHESIS

BACKGROUND OF THE INVENTION

This invention is an endoluminal prosthesis to be used in passageways or conduits of the human body, such as to restore the passage in blood vessels that have been narrowed or blocked by diseases such as a stenosis.

The present endoluminal prosthesis is particularly suitable for use in the vicinity of a bifurcation, mainly of the carotid artery.

The present invention also relates to that type of endoluminal prostheses which are self-expanding, such as those made of superelastic or shape memory material, such as Nitinol.

The present invention also relates to endoluminal prostheses provided with means for enabling prompt location thereof, such as by means of radioscopy.

Endoluminal prosthesis, particularly of the self-expanding type, are known for example from U.S. Pat. Nos. 4,665,771, 4,665,905, 4,925,445, EP-A-0928606, or WO 2005/104991.

Though being acceptable in many respects, particularly for their great flexibility and resilience, which enable them to be easily positioned in narrow and tortuous passages in their collapsed state, these endoluminal prostheses, in some cases, are not sufficiently suitable, when expanded, to support the vessel walls, in order to maintain a proper free lumen for the blood to pass therethrough.

Furthermore, in some cases the complex geometry of such known stents may be harmful, since it can hang up on or pinch the vessel wall, thus favoring the re-forming of obstructions, such as plaques and stenosis.

Particularly, in the carotid, the endoluminal prosthesis must ensure a considerable radial strength in the middle portion thereof, or generally in the portion positioned at the stenosis. Furthermore, the endoluminal prosthesis must be made with the least amount of material as possible, mainly in the end portions, or generally in those portions that are positioned outside the stenosis. In fact, it has been estimated that the ratio of the metal and the artery must remain within well defined limits, about 15%. Too high values lead to restenosis and high mechanical rigidity.

SUMMARY OF THE INVENTION

The object at the heart of the present invention is to provide an endoluminal prosthesis, having such structural and functional characteristics to overcome the drawbacks mentioned with reference to the prior art and meet the requirements thereby obtaining the best results for both.

This object is solved by means of an endoluminal prosthesis as described below.

BRIEF DESCRIPTION OF THE DRAWINGS

Further characteristics and the advantages of the prosthesis according to the invention will become apparent from the description given below of embodiments thereof, being merely illustrative and non-limiting, with reference to the annexed figures, in which.

DETAILED DESCRIPTION OF THE INVENTION

With reference to the above mentioned figures, numeral 500 generally indicates an endoluminal prosthesis, such as a prosthesis of the self-expanding type for ducts or vessels of living bodies, particularly for application in the carotid, at the bifurcation.

Figures 4, 4A:
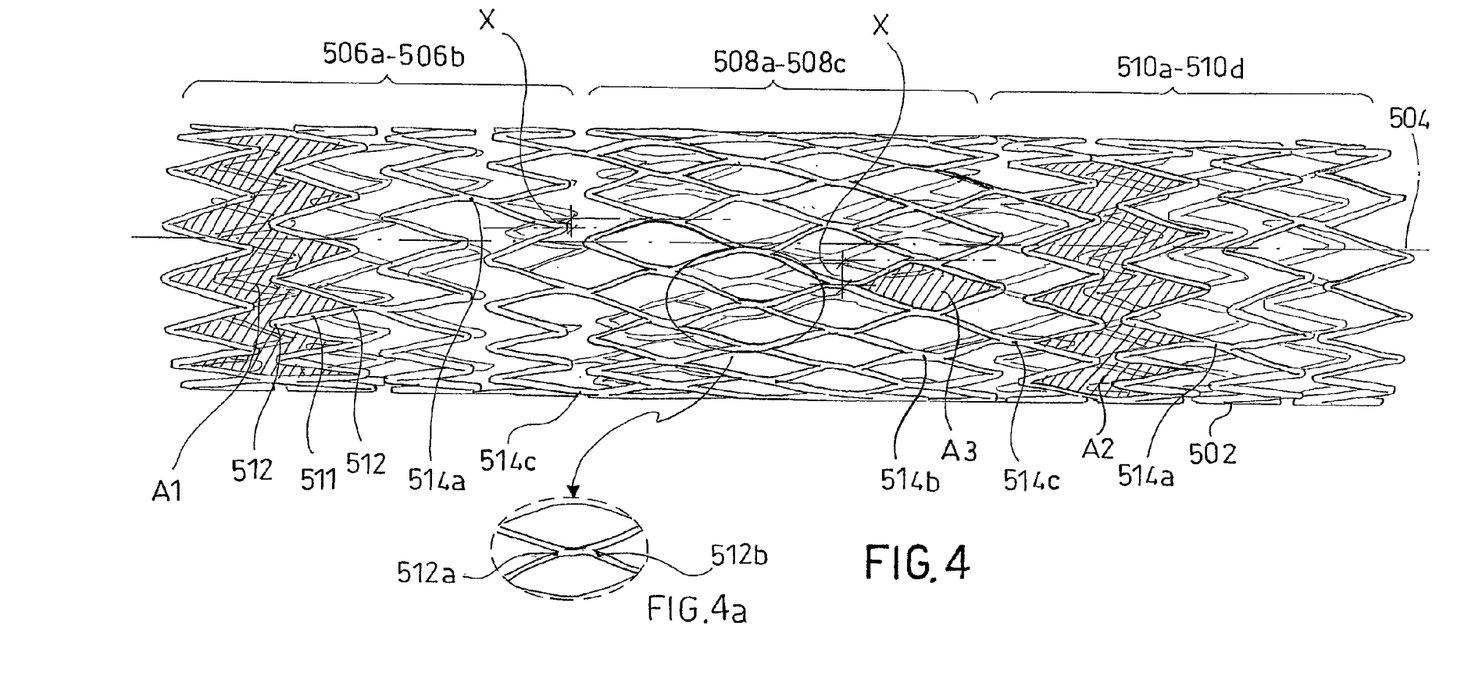
FIG. 4 illustrates, in a perspective view, the prosthesis from FIG. 1 in the expanded condition.
FIG. 4a illustrates an enlargement of a detail from FIG. 4.
Figure 5:
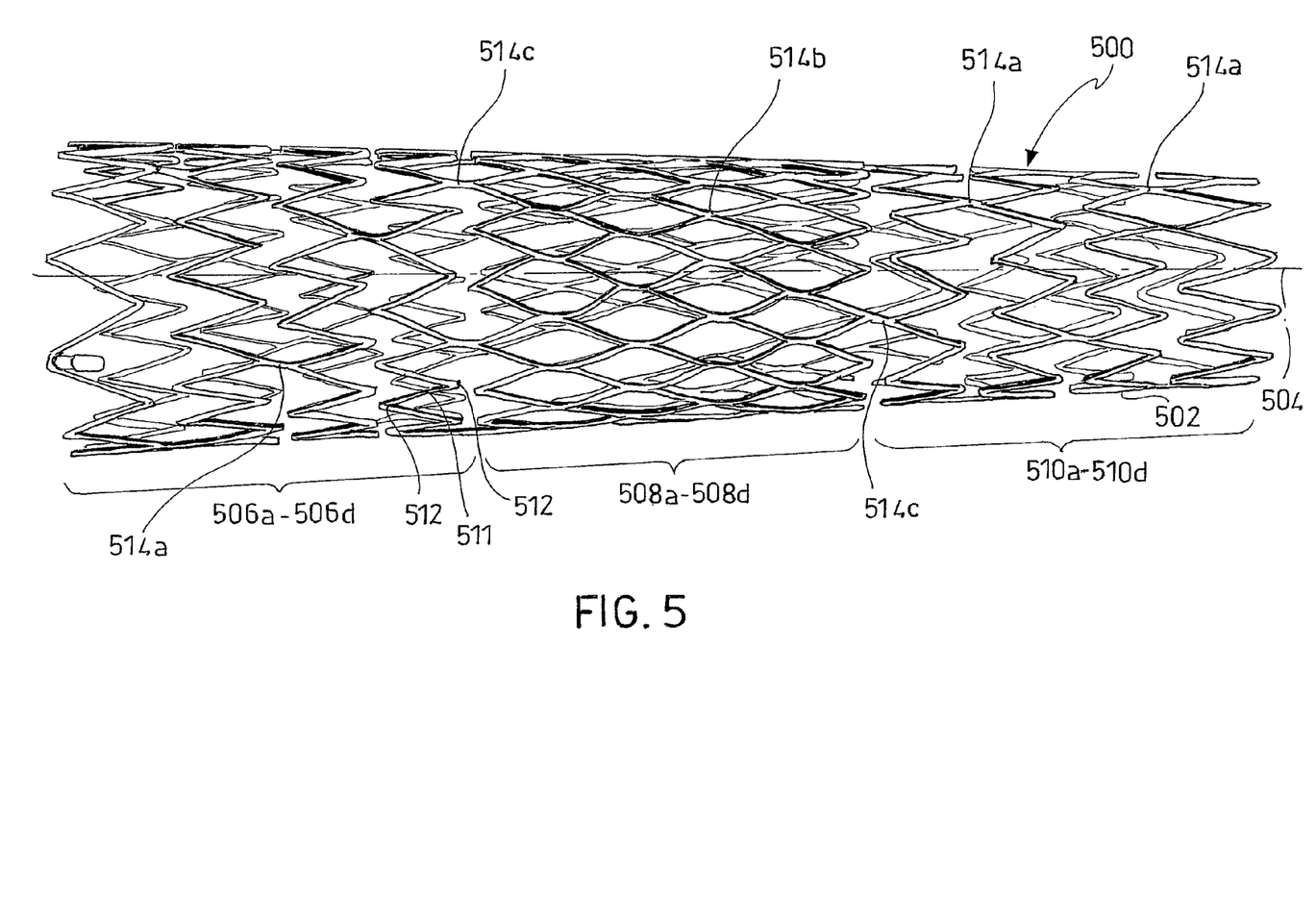
FIG. 5 illustrates, in a perspective view, a possible variant embodiment of the prosthesis of FIG. 4.

In accordance with a general embodiment of the present invention, the endoluminal prosthesis comprises a tubular body 502 suitable to turn from a collapsed condition to an expanded or partially expanded condition (FIG. 4 or 5).

By "collapsed condition" is meant a state of the prosthesis as being contracted such as to have a smaller bulk than in an operating use condition, e.g. a condition where the tubular body 502 has smaller size or outer diameter than in an operating use condition. For example, the prosthesis is arranged in a collapsed condition when it is either accommodated or arranged on a transport and delivery device suitable to travel along a duct or vessel to the area to be treated. For example, in the case of a self-expanding prosthesis, this is accommodated in a sheath such as to be maintained in the collapsed condition.

By "expanded or partially expanded condition" is meant a condition where the prosthesis is free from restrictions or an operating use condition with the prosthesis being widened upon pressure contact against the inner surfaces of duct or vessel walls (FIGS. 4 and 5).

The tubular body 502 extends along a longitudinal axis 504.

By "longitudinal axis" is meant for example either a symmetry axis of a cylindrical body or the stretch axial direction of a tubular body.

The tubular body 502 comprises a plurality of serpentines 506a-506d, 508a-508e, 510a-510d, or closed meander paths, extending along a substantially circumferential direction.

By "serpentine" is meant an element that develops zig-zag/to-and-fro around a main direction of stretching.

Each of the serpentines comprises arm portions, or arms 511.

Each of the serpentines comprises bend portions, or bends 512, joining two subsequent arms 511 to form the meander path.

With further advantage, the bends 512 facing an adjacent serpentine are circumferentially offset relative to the respective and opposite bends 512 of the adjoining serpentine, both when the prosthesis is collapsed and when the prosthesis is expanded or partially expanded.

In other words, considering a tract of a first serpentine corresponding to a pitch, the adjacent serpentine is offset X up to about half pitch (FIG. 4). With a half-pitch offset, two adjacent serpentines are substantially mirror symmetric about a middle circumferential line between the two serpentines.

In accordance with a possible embodiment, the arms are connected by bends such as to form a sequence of peaks and valleys along the circumferential direction of the corresponding serpentines. With a half-pitch offset, to a bend of a first serpentine defining a peak 512a there corresponds a bend of the adjacent serpentine defining a valley 512b, "peak" and "valley" meaning the substantially sinusoidal development of the serpentine (FIG. 4a). Two respective peaks and valleys of two adjacent serpentines define a pair of bends located at the shortest longitudinal distance between the two serpentines.

Advantageously, at least one bridge 514a-514c, of main longitudinal extension, connects two adjacent serpentines. Particularly, the bridge connects two adjacent serpentines at two respective bends being at the shortest longitudinal distance between the two serpentines.

Preferably, the at least one bridge 514a-514c connecting adjacent serpentines extends substantially rectilinear.

Advantageously, the serpentines are grouped in at least two portions 506 and 510, 508 arranged along the longitudinal axis 504, in which a first portion 506 or 510 comprises at least two adjacent serpentines interconnected by at least one bridge 514a. In the first portion 506 or 510 at least one pair of bends at the shortest longitudinal distance between the two adjacent serpentines is not connected by a bridge.

A second portion 508 comprises at least two adjacent serpentines interconnected by bridges 514b equal in number to the pairs of bends of the two serpentines being at the shortest longitudinal distance between the two serpentines. In other words, all the bends of a first serpentine facing the adjacent serpentine are connected to all the bends of the adjacent serpentine that face the first serpentine by means of a respective bridge 514b.

Preferably, the first portion is a distal and/or proximal end portion of the endoluminal prosthesis and the second portion is a middle portion of the endoluminal prosthesis.

Figure 1:
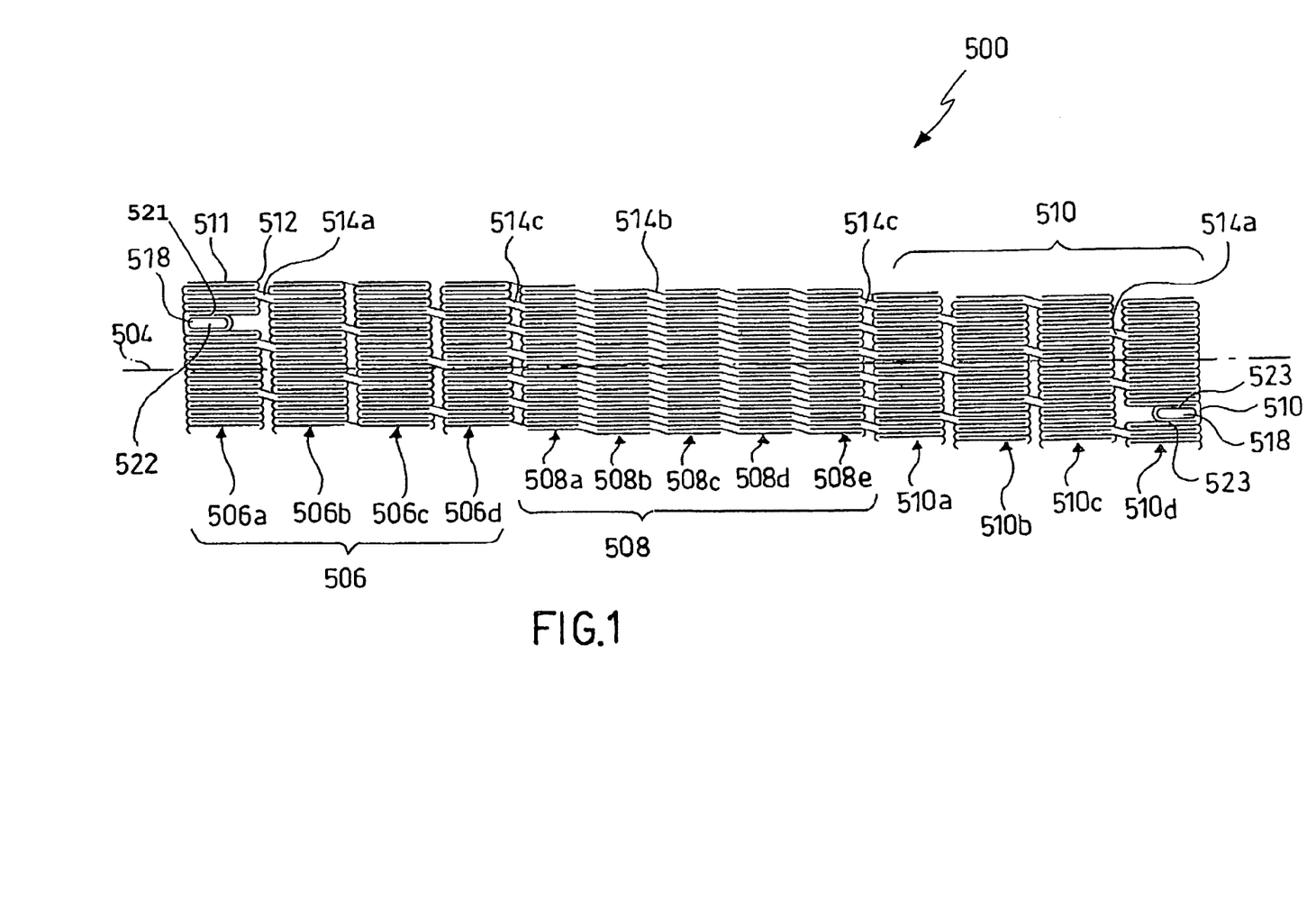
FIG. 1 illustrates a plane development of a possible embodiment of an endoluminal prosthesis according to the present invention, illustrated in the collapsed or non-expanded condition.

The example from FIG. 1 comprises three portions, two first portions 506 and 510 and a second portion 508, respectively.

The end portion designated with 506 comprises the serpentines indicated with 506a-506d and corresponds to the first portion described above. In fact, two adjacent serpentines along the longitudinal axis 504 (for example, the serpentine 506a and the serpentine 506b) are interconnected by at least one bridge 514a. Several pairs of bends being at the shortest longitudinal distance between the two adjacent serpentines 506a and 506b are not connected by a bridge. In the example from FIG. 1, three bridges 514a are provided, which join two adjacent serpentines (506a and 506b, or 506b and 506c, or 506c and 506d) of the first portion 506. Furthermore, between two subsequent bridges 514a in the circumferential direction there are provided five pairs of bends situated at the shortest longitudinal distance between the two adjacent serpentines and not connected by a bridge. Considering the arms and bends between two subsequent bridges 514a in the circumferential direction a cell or perimeter is obtained that comprises at least one pair of bends (five, in the case of FIG. 1) which are situated at the shortest longitudinal distance between the two adjacent serpentines and not connected by a bridge (in FIG. 4, the cell or perimeter defines the dotted area A1).

Again, considering FIG. 1, the portion designated with 506 is an end portion (that can be either proximal or distal, since the prosthesis in the expanded configuration has a substantially cylindrical conformation).

In addition, in FIG. 1 the prosthesis comprises a further first portion, such as described above, that is defined by the end portion designated with 510 comprising the serpentines designated with 510a-510d. What has been described above with reference to the portion 506 in FIG. 1 can be applied thereto. The respective bridges between the two adjacent serpentines (such as the serpentine 510c and the serpentine 510d) have been designated with 514a. Also in this case, the portion designated with 510 is an end portion (that can be either proximal or distal, since the prosthesis in the expanded configuration has a substantially cylindrical conformation). With reference to FIG. 4, with A2 has been designated the area enclosed by the cell or perimeter defined between two subsequent bridges 514a in the circumferential direction and comprising at least one pair of bends (five, in the case of FIG. 1 or 4) which are situated at the shortest longitudinal distance between the two adjacent serpentines and not connected by a bridge.

In accordance with what has been described in general terms, the prosthesis in FIG. 1 further comprises a portion designated with 508 comprising, in turn, the serpentines designated with 508a-508e. This portion 508 corresponds to the second portion described above. In fact, two adjacent serpentines along the longitudinal axis 504 (for example, the serpentine 508a and the serpentine 508b) are interconnected by a number of bridges 514b equal to the number of pairs of bends of the two serpentines situated at the shortest longitudinal distance between the two serpentines. In other words, all the bends of a first serpentine 508a facing the adjacent serpentine are connected to all the bends of the adjacent serpentine 508b that face the first serpentine 508a.

In the case of FIG. 1, the portion 508 is a middle portion of the endoluminal prosthesis that is interposed between the end portion 506 and the end portion 510.

Considering the arms and the bends between two subsequent bridges 514b in the circumferential direction a cell or perimeter is obtained, which comprises four arms (belonging two-by-two to one of the two adjacent serpentines), a pair of bends situated at the longest longitudinal distance between the two adjacent serpentines and two bridges 514b (in FIG. 4, the cell or perimeter defines the dotted area A3).

Figure 2:
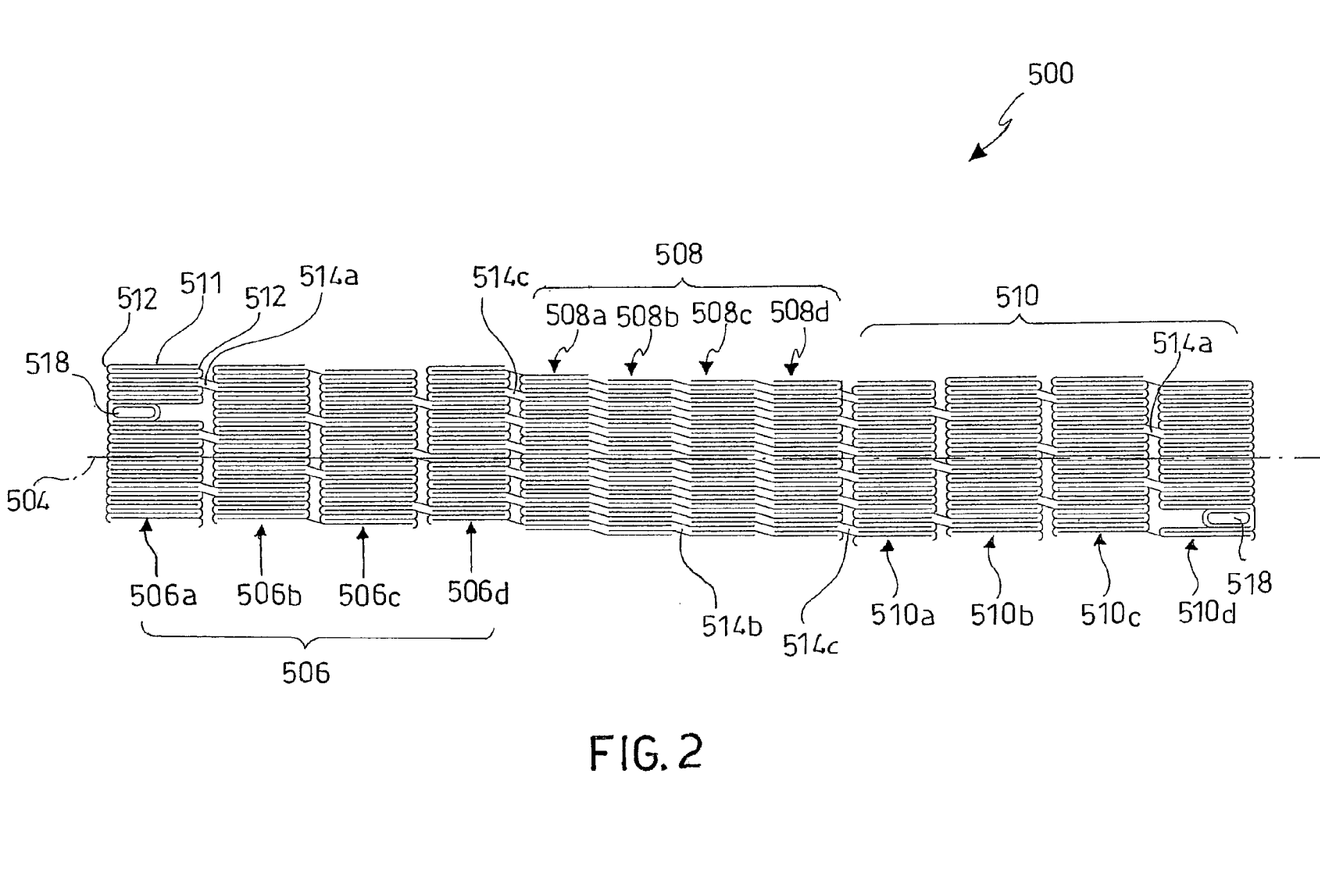
FIGS. 2 and 3 illustrate a plane development of a variant embodiment of the prosthesis from FIG. 1, illustrated in a collapsed or non-expanded condition.

FIG. 2 is substantially similar to above-described FIG. 1 except that both the end portion 506 defining a first portion, and the end portion 510 also defining a first portion, and the middle portion 508 defining a second portion comprise four serpentines 506a-506d, 510a-510d, 508a-508d, respectively.

Figure 3:
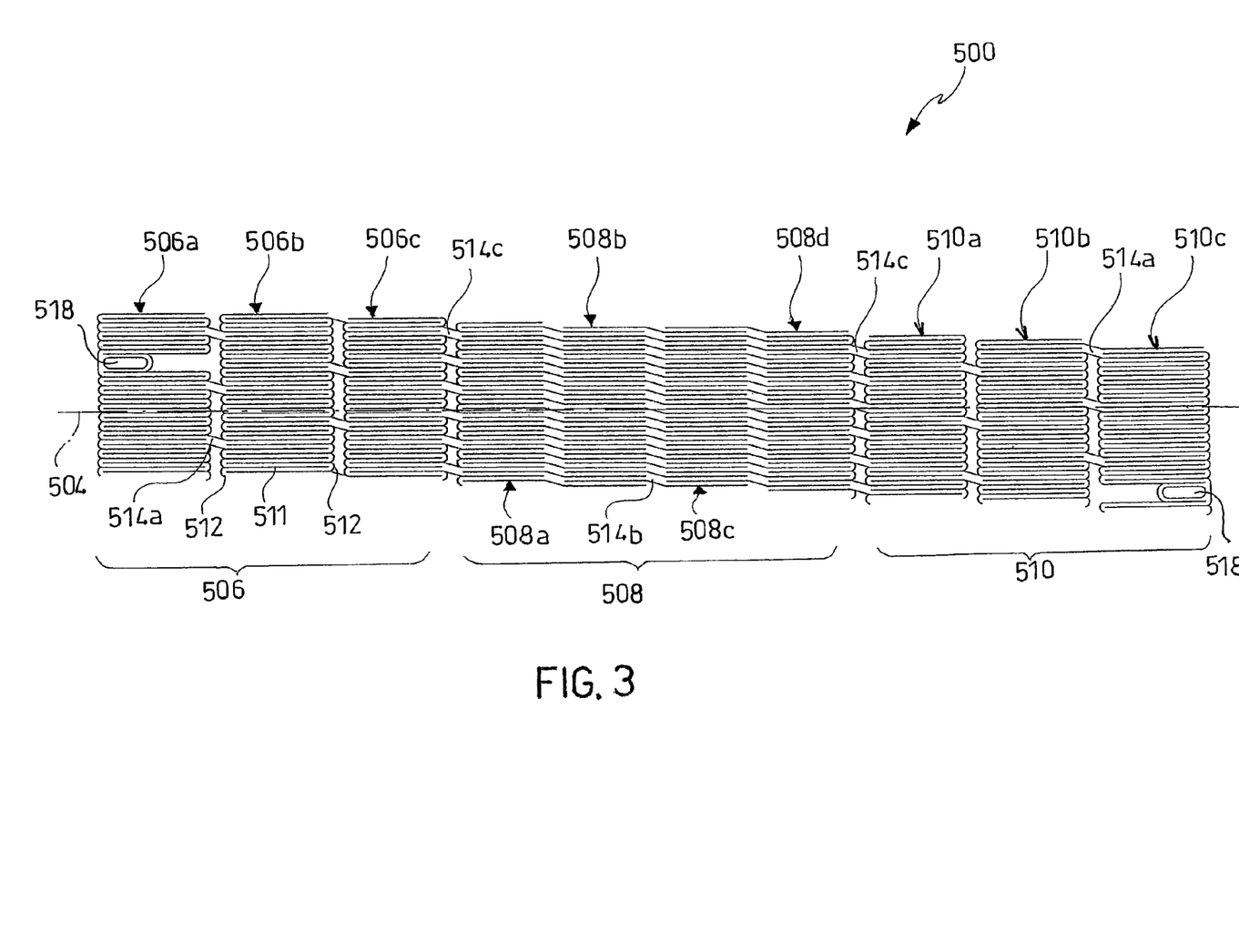

FIG. 3 is also substantially similar to above-described FIG. 1 except that both the end portion 506 defining a first portion, and the end portion 510 also defining a first portion, comprise three serpentines 506a-506c, 510a-510c, respectively, whereas the middle portion 508 defining a second portion comprises four serpentines 508a-508d.

FIG. 4 illustrates the prosthesis from FIG. 1 in the expanded configuration, whereas FIG. 5 illustrates a prosthesis that, in the expanded configuration, has the shape of a truncated cone, though having the same arrangement of portions and serpentines as the prosthesis in FIG. 1.

In accordance with a possible embodiment, the first and second serpentine portions are connected by bridges 514c that join pairs of bends of the two serpentines situated at the shortest longitudinal distance between the two serpentines, each being a part of one of the two portions. Advantageously, the bridges 514c that join the first and second portions are in a number comprised between the number of the bridges 514a connecting two adjacent serpentines of the first portion and the number of bridges 514b connecting two adjacent serpentines of the second portion. In accordance with a possible embodiment, the bridges 514c joining the first and second portions are about twice the bridges 514a connecting two adjacent serpentines of the first portion.

With reference to FIG. 1, with 514c have been designated the bridges joining the end portion 506 to the middle portion 508 (particularly, the serpentine 506d and the serpentine 508a) and the middle portion 508 to the other end portion 510 (particularly, the serpentine 508e and the serpentine 510a). Advantageously, the bridges 514c are in a number comprised between the number of the bridges 514a connecting two adjacent serpentines of the first portion (end portion 506 or 510) and the number of bridges 514b connecting two adjacent serpentines of the second portion (or middle portion (508). Preferably, as illustrated in FIG. 1, the bridges 514c joining the first and second portions are about twice (six) the bridges 514a connecting two adjacent serpentines of the first portion.

FIGS. 2 and 3 are similar in connection with this aspect.

In accordance with a possible embodiment, the first portion 506 or 510 comprises at least two, preferably at least three serpentines and the bridges 514a connecting two adjacent serpentines are circumferentially offset relative to the immediately subsequent bridges along the longitudinal axis. An example of this arrangement is illustrated in FIG. 1-3, for example with reference to the bridges connecting the serpentines 506a and 506b that are circumferentially offset relative to the immediately subsequent bridges connecting the serpentines 506b and 506c. A similar arrangement is provided for the portion 510.

Preferably, the first portion is a proximal portion of the endoluminal prosthesis and comprises at least one marker or radiopaque element 518. Furthermore, the first portion is also a distal portion of the endoluminal prosthesis and comprises at least one marker or radiopaque element 518.

Preferably, the endoluminal prosthesis comprises a proximal portion 506 provided as the first portion, a middle portion 508 provided as the second portion and a distal portion 510 provided as the first portion. Advantageously, both in the collapsed and in the expanded condition each proximal, middle and distal portion develops by about one third of the length of the endoluminal prosthesis.

According to a possible example, the prosthesis comprises a proximal portion 506 provided as the first portion, a middle portion 508 provided as the second portion and a distal portion 510 provided as the first portion. In addition, the distal portion 510 and the proximal portion 506 comprise four serpentines, respectively, and the middle portion comprises five serpentines (FIG. 1).

According to a different example, the prosthesis comprises a proximal portion 506 provided as the first portion, a middle portion 508 provided as the second portion and a distal portion 510 provided as the first portion. Furthermore, the distal portion, the middle portion and the proximal portion comprise four serpentines, respectively (FIG. 2).

According to a further different exemplary embodiment, the prosthesis comprises a proximal portion 506 provided as the first portion, a middle portion 508 provided as the second portion and a distal portion 510 provided as the first portion. In addition, the distal portion and the proximal portion comprise three serpentines, respectively, and the middle portion comprises four serpentines (FIG. 3).

Particularly, it is advantageous to provide that in a prosthesis comprising a proximal portion 506 provided as the first portion, a middle portion 508, arranged as the second portion and a distal portion 510 arranged as the first portion, the distal portion and the proximal portion comprise a number of serpentines less than or equal to the central portion.

In accordance with a possible embodiment, the bridges 514a-514c are rectilinear and slightly inclined relative to the longitudinal axis. Preferably, all the bridges are inclined in the same direction relative to the longitudinal axis. Even more preferably, all the bridges are parallel to each other.

In accordance with a possible embodiment, the prosthesis defines a cylindrical tubular body in the expanded condition (FIG. 4). In accordance with a different embodiment, the endoluminal prosthesis defines a truncated-cone-shaped tubular body in the expanded condition (FIG. 5).

In accordance with a possible embodiment, the width of the bridges as measured substantially in the circumferential direction is about twice the width of the arms, also measured substantially in the circumferential direction. This aspect can be advantageously observed with reference to all the bridges in the prosthesis, i.e. with reference to the bridges of the first portion, second portion or the bridges connecting two different portions.

In several exemplary embodiments, the radial compression strength has been measured (N). Several values are reported in FIG. 7a.

Generally, the second portion 508 is capable of withstanding a compression force ranging between 0.10 and 0.20 N. In addition, the first portion 506 or 510 is capable of withstanding a compression force ranging between 0.04 and 0.06 N.

Figure 7A:
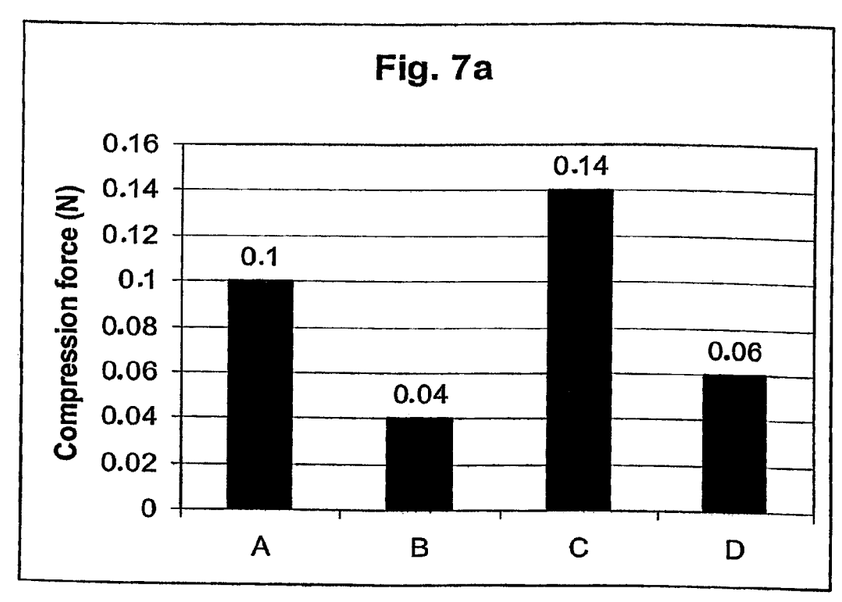
FIG. 7a illustrates diagrams of the radial compression force (N) of the distal, middle and proximal portion of two prostheses according to FIG. 5 as compared with a prior art prosthesis.
Figure 8:
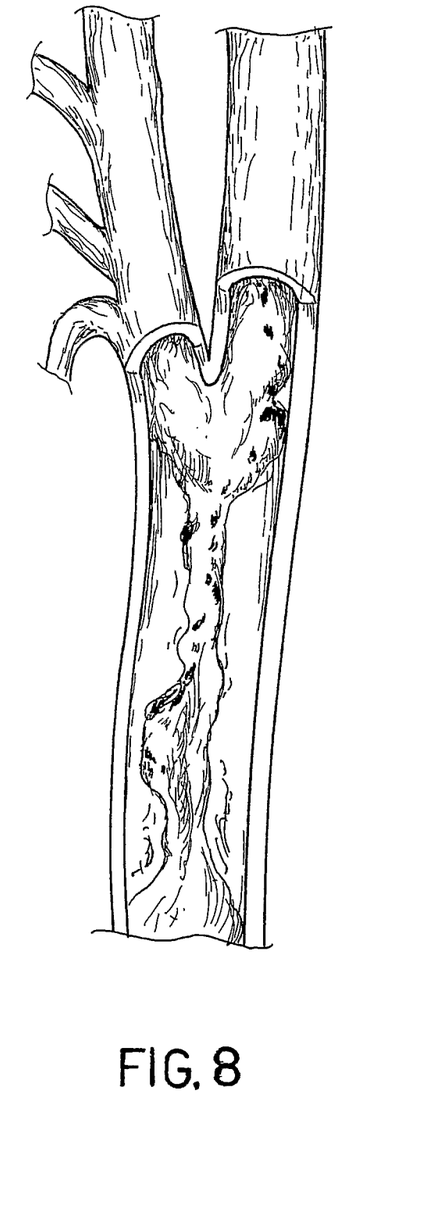
FIG. 8 illustrates a carotid portion to which the prosthesis according to the present invention is advantageously applied.

For example, FIG. 7a relates to a tubular truncated-cone-shaped body with a diameter of 6-9 mm and 30 mm in length. The first value A corresponds to the prior art (without differentiation in the radial force along the longitudinal direction). The other values B, C, D correspond to the distal, middle, and proximal portion of the prosthesis, respectively. In the instant case, A=0.10N, B=0.04N, C=0.14N and , D=0.06N.

Figure 6A:
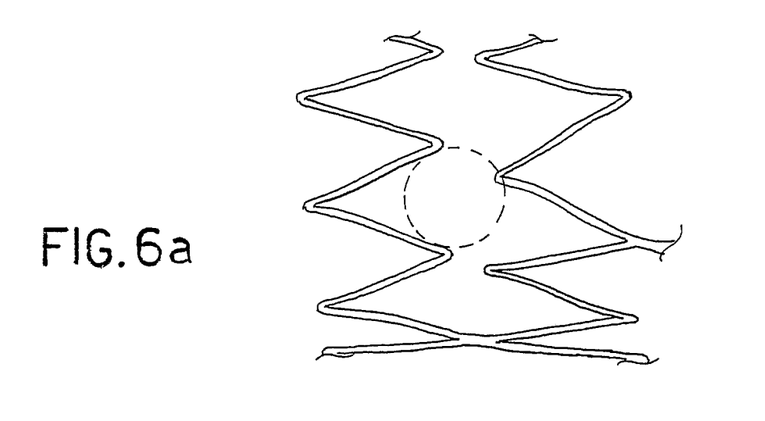
FIG. 6a-6c illustrates an enlarged detail of the prosthesis from FIG. 5, at a distal, middle and proximal portion, respectively.
Figure 6B:
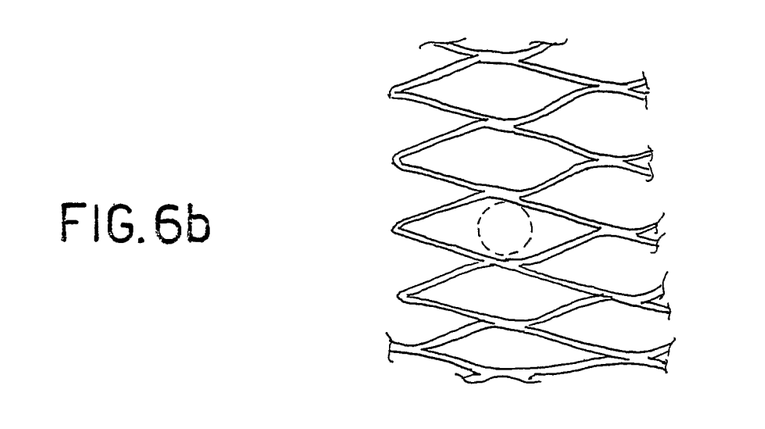
Figure 6C:
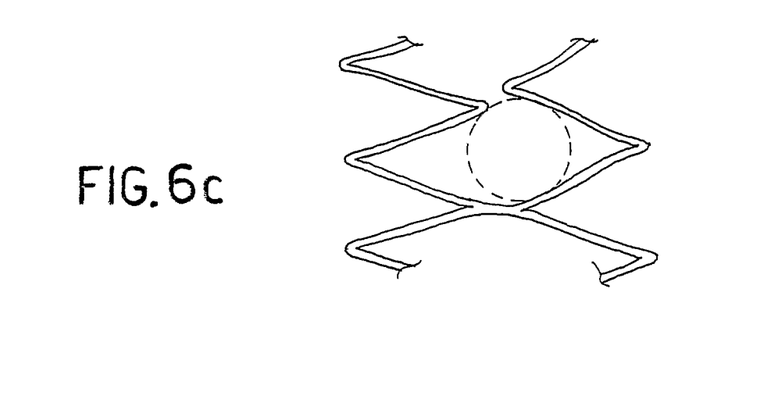

FIG. 6a-6c illustrate a further characteristic of a prosthesis according to the present invention defined as "scaffolding" with reference to the proximal 506, middle 508 and distal 510 portion of the prosthesis, respectively. This characteristic is connected to the geometry of the stent and the support capacity of the latter. This characteristic can be indicated by measuring the diameter of the maximum circumference inscribed within a cell. The value is about 2 mm for the second portion and about 1 mm for the first portion. The lower this value, the closer the serpentines, the support being thereby increased.

The configuration as described allows obtaining an optimum ratio of the metal extension and the artery, expressed as a percentage. Preferably, this value expressed as a percentage is the same in the end portions and different in the middle with reference to the example illustrated above. The values of the proximal and distal portions are relatively low. The middle portion value is slightly greater, but, however, sufficiently low to avoid a wide contact area between the prosthesis material and the vessel tissue.

Furthermore, with reference to the flexibility, meaning the capacity of bending and assume a circular shape without breaking, it has been seen that the second portion (middle portion) is advantageously rather rigid, whereas the first portion/s (end portions or distal and proximal portions) are rather flexible. This allows the stent to be more easily guided to the position where it has to be implanted.

The present invention also relates to the use of an endoluminal prosthesis as described above that can be implanted at a bifurcation, particularly in the carotid. The prosthesis in the expanded condition can have the shape of a truncated cone and a distal portion of the prosthesis having a smaller circumference than the opposite proximal portion is positioned at the bifurcation.

In accordance with an embodiment, the prosthesis 500 is made as one piece. For example, the body 502 is obtained by cutting a tubular element, preferably by means of laser cutting.

Advantageously, the body is made of a superelastic material. In accordance with a different embodiment, the body is made of a strain hardened pseudoelastic material. In other words, a material being in the austenitic state at room temperature (Af<15° C.) when annealed can be used, to which a sufficient strain hardening is then applied, such as greater than 30%, which allows to get 3%-4% elastic recovery after deformation or more. Preferably, 50% strain hardening is applied.

In accordance with an embodiment, the body 502 is made of a shape memory material.

Advantageously, the body is made of Nitinol, or a Ni and Ti based alloy, such as with Nickel nominal weight percentage of 55.8%.

For example, a material with Austenite-to-Martensite phase transition can be used that, when being in the annealed or stress-relieved state, during a heating of the same, the highest temperature at the end of the transformation into austenite, or Af, is lower than 15° C.

In accordance with an embodiment, in order to form the marker 518, the first serpentine 506*a* and/or the last serpentine 510*d* comprises at least one frame 521 defining a slot or housing 522. The frame 521 is arranged at a bend between two arms. Particularly, the frame 521 and the slot 522 can be arranged in place of at least two arms and one bend relative to the immediately adjacent serpentines along the longitudinal axis.

According to a possible embodiment, the second serpentine and the third serpentine comprise the same number of arms and the same number of bends.

Preferably the frame 521 and the slot 522 are arranged at the bend between two arms in place of four arms and three bends relative to the second or third serpentines. Advantageously the frame 521 totally occupies the width cleared by the replaced arms and bends, as measured along the circumferential direction, when the endoluminal prosthesis is in the collapsed condition.

In accordance with a possible embodiment, the slot or housing 522 passes all through the thickness of the tubular body 502.

Advantageously the frame 521 is arranged in the concave part of the bend between the two arms that are directly connected to the frame 521.

According to a possible embodiment, the prosthesis is formed as one piece from a tubular body 502 by means of cutting, such as laser cutting of a cylindrical wall thereof.

Advantageously, the frame 521 is formed as one piece in the tubular body 502 obtained by means of laser cutting of a cylindrical wall.

In accordance with a possible embodiment, the slot 522 has an elongated shape in the direction of the longitudinal axis of the prosthesis, preferably elliptical or rectangular with short rounded sides. Advantageously, the frame 521 has an elongated shape in the direction of the longitudinal axis of the prosthesis. Preferably the short side of frame 521 corresponding to the bend between both arms that are directly connected to the frame is substantially rectilinear in the circumferential direction, when considered in a plane development of the prosthesis.

Advantageously, the two arms that are directly connected to the frame 521 join to the frame at end points.

Advantageously the frame 521 comprises two elongated sides 523 having substantially the same width as the arms 511 of the prosthesis, as measured along the circumferential direction, and a shorter length than the arms 511 of the prosthesis, as measured along the longitudinal direction 504.

Advantageously, a radiopaque material is provided within the slot 522, preferably welded or melted within the slot. The radiopaque material may be any material having a greater visibility to X-rays than the material used for the prosthesis.

In the case where the prosthesis is made of a superelastic or shape memory material, such as Nitinol (or an alloy with Ni and Ti as the main part), the radiopaque material can be selected from Tantalum, Gold, Platinum, Tungsten or other materials suitable for the purpose and clearly biocompatible.

According to a possible embodiment, the first serpentine 506*a* housing the frame 521 is an end serpentine of the prosthesis. Advantageously, both end serpentines of the prosthesis, i.e. the first and the last serpentines, comprise at least one frame 521, respectively.

From what has been stated above, it may be appreciated how providing an endoluminal prosthesis according to the present invention allows to meet such contrasting requirements as having a high strength to radial compression force in the middle of the prosthesis, while avoiding having to excessively increase the amount of material in that area.

Furthermore, a good level of flexibility is obtained on the sides, while a more undeformed shape is maintained in the middle.

These aspects are particularly advantageous with respect to the carotid, which may be subjected to impacts or compressions due to its location. In fact, the prosthesis according to the present invention ensures that the carotid channel will be opened also in the event of impact or compression, since the prosthesis withstands compression at least in the middle thereof, follows the deformation of the carotid, and however ensures a passage lumen.

Due to the prosthesis provided, endoluminal operations can be carried out in tortuous vessels or ducts, and at the same time, an optimum and constant support of the treated vessel wall can also be ensured when the prosthesis is in the expanded state.

Particularly advantageous is the provision and shape of the markers, which make the prosthesis visible and easily positionable, without interfering with the delicate geometries involved, which are suitably designed for ensuring the above-mentioned results.

It should be understood that variations and/or additions may be provided to what has been described and illustrated above.

The number of serpentines, arms or bends may vary from what has been described or illustrated. The serpentine shape may also vary.

Generally all the embodiments which have been described as being feasible above can be made as such in the absence of those characteristics described as belonging to other possible embodiments.

In accordance with a possible embodiment, the prosthesis can be coated with a coating material, such as PTFE, biodegradable material, polyester fibers, polyurethane, or the like.

To the embodiments of the endoluminal prosthesis described above, those skilled in the art, aiming at satisfying contingent and specific needs, may carry out a number of modifications, variants and replacements of elements with others functionally equivalent, without departing from the scope of the claims below.

What is claimed is:

1. An endoluminal prosthesis comprising:
   a tubular body adapted to turn from a collapsed state to an expanded state,
   said tubular body extending along a longitudinal axis,
   said tubular body comprising a plurality of serpentines, or closed meander paths, extending along a substantially circumferential direction, and at least one bridge connecting adjacent serpentines, each of said serpentines comprising arm portions, or arms, and bend portions, or bends which join two subsequent arms to form said serpentine or meander path, wherein each bend of a serpentine facing an adjacent serpentine is circumferentially offset relative to all bends of the adjacent serpentine, both when the tubular body is in the collapsed state and when the tubular body is in the expanded state, wherein said serpentines are grouped in at least two portions arranged along said longitudinal axis, wherein a first portion comprises at least two adjacent serpentines interconnected by at least one bridge connecting a first bend of a first serpentine of the at least two adjacent serpentines to a second bend of a second serpentine of the at least two adjacent serpentines, wherein the second bend is the bend of the second serpentine nearest to the first bend, wherein at least one bend of the first serpentine facing the second serpentine is not connected by a bridge to any bends of the second serpentine facing the first, and wherein a second portion comprises at least two adjacent serpentines wherein each bend of a first serpentine of the at least two adjacent serpentines facing a second serpentine of the at least two serpentines is connected by a bridge to a corresponding adjacent bend of the second serpentine facing the first serpentine which is the nearest distance from the corresponding bend of the first serpentine.

2. The endoluminal prosthesis according to claim 1, wherein said first portion is a distal and/or proximal end portion of said endoluminal prosthesis and said second portion is a middle portion of said endoluminal prosthesis, 3. The endoluminal prosthesis in accordance with claim 1, wherein said first and second serpentine portions are connected by bridges that join pairs of bends of the two serpentines situated at the shortest longitudinal distance between the two serpentines, each being a part of one of the two portions.

4. The endoluminal prosthesis according to claim 3, wherein the bridges that join the first and second portions are in a number between the number of the bridges connecting two adjacent serpentines of the first portion and the number of bridges connecting two adjacent serpentines of the second portion.

5. The endoluminal prosthesis according to claim 1, wherein the first portion comprises at least three serpentines and wherein the bridges connecting two adjacent serpentines are circumferentially offset relative to the immediately subsequent bridges according to the longitudinal axis.

6. The endoluminal prosthesis according to claim 1, wherein said first portion is a proximal portion of the endoluminal prosthesis and comprises at least one radiopaque marker or element.

7. The endoluminal prosthesis according to claim 1, wherein said first portion is a distal portion of the endoluminal prosthesis and comprises at least one radiopaque marker or element.

8. The endoluminal prosthesis according to claim 1, wherein the tubular body comprises a proximal portion provided as said first portion, a middle portion provided as said second portion and a distal portion provided as said first portion, wherein both in the collapsed state and in the expanded state, each of said proximal portion, middle portion, and distal portion have a length that is about one third of a length of the tubular body.

9. The endoluminal prosthesis according to claim 1, wherein the tubular body comprises a proximal portion provided as said first portion, a middle portion provided as said second portion, and a distal portion provided as said first portion, wherein said distal portion and said proximal portion each have four serpentines, and wherein said middle portion has five serpentines.

10. The endoluminal prosthesis according to claim 1, wherein the tubular body comprises a proximal portion provided as said first portion, a middle portion provided as said second portion, and a distal portion provided as said first portion, wherein said distal portion and said proximal portion each has three serpentines, and wherein said middle portion has four serpentines.

11. The endoluminal prosthesis according to claim 1, wherein the tubular body comprises a proximal portion provided as said first portion, a middle portion provided as said second portion, and a distal portion provided as said first portion, wherein said distal portion and said proximal portion each have a number of serpentines less than or equal to a number of serpentines of said middle portion.

12. The endoluminal prosthesis according to claim 1, wherein the tubular body is a cylinder shape in the expanded state.

13. The endoluminal prosthesis according to can herein the tubular body is a truncated cone shape in the expanded state.

14. The endoluminal prosthesis according to claim 1, further comprising a coating material.

15. The endoluminal prosthesis according to claim 14, wherein said coating material is PTFE.

16. The endoluminal prosthesis according to claim 14, wherein said coating material is a biodegradable material.

17. The endoluminal prosthesis according to claim 14, wherein said coating material comprises polyester fibers.

18. The endoluminal prosthesis according claim 1, wherein a width of the bridges as measured substantially in the circumferential direction is about twice a width of the arms, also measured substantially in the circumferential direction.

19. The endoluminal prosthesis according to claim 1, wherein said prosthesis can be implanted at a bifurcation.

20. The endoluminal prosthesis according to claim 19, wherein said prosthesis in the expanded condition is truncated-cone shaped and wherein a distal portion of said prosthesis having a smaller circumference than the opposite proximal portion is positioned at the bifurcation.

21. The endoluminal prosthesis according claim 6, wherein said at least one radiopaque marker or element comprises a frame that takes the space of four of said arms.

* * * * *

UNITED STATES PATENT AND TRADEMARK OFFICE
CERTIFICATE OF CORRECTION

PATENT NO.       : 8,778,010 B2                    Page 1 of 1
APPLICATION NO.  : 12/159649
DATED            : July 15, 2014
INVENTOR(S)      : Venturelli et al.

It is certified that error appears in the above-identified patent and that said Letters Patent is hereby corrected as shown below:

In the claims,

In the Claim 2, column 9, line 35
"portion of said endoluminal prosthesis," should read -- "portion of said endoluminal prosthesis." --

In the Claim 13, column 10, line 33
"prosthesis according to cam herein the" should read -- "prosthesis according to claim 1, wherein the" --

In the Claim 18, column 10, line 43
"prosthesis according claim 1, wherein" should read -- "prosthesis according to claim 1, wherein" --

In the Claim 20, column 10, lines 50, 51
"condition is truncated-cone shaped and" should read -- "condition is truncated cone-shaped and" --

In the Claim 21, column 10, line 54
"prosthesis according claim 6, wherein" should read -- "prosthesis according to claim 6, wherein" --

Signed and Sealed this
Twenty-first Day of July, 2015

Michelle K. Lee
*Director of the United States Patent and Trademark Office*